United States Patent
Picard et al.

(10) Patent No.: US 6,297,204 B1
(45) Date of Patent: *Oct. 2, 2001

(54) TWO-PHASE COSMETIC AND/OR DERMATOLOGIC COMPOSITION WHICH IS USEFUL IN PARTICULAR FOR REMOVING MAKE-UP FROM THE EYES

(75) Inventors: Elisabeth Picard, Velizy; Catherine Marion, Sceaux, both of (FR)

(73) Assignee: L'Oreal, Paris (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/346,168

(22) Filed: Jul. 1, 1999

(30) Foreign Application Priority Data

Jul. 1, 1998 (FR) .................................................. 98 08417

(51) Int. Cl.$^7$ ............................... C11D 3/43; C11D 3/44; C11D 3/48
(52) U.S. Cl. .................. 510/136; 510/119; 510/130; 510/137; 510/242; 510/319; 510/382; 510/417
(58) Field of Search .................................... 510/136, 119, 510/130, 137, 242, 319, 382, 417

(56) References Cited

U.S. PATENT DOCUMENTS

| | | | | |
|---|---|---|---|---|
| 4,405,645 | * | 9/1983 | Rothlisberger et al. | 424/326 |
| 4,478,821 | * | 10/1984 | Carrillo | 424/47 |
| 5,141,803 | * | 8/1992 | Pregozen | 428/288 |
| 5,500,217 | * | 3/1996 | Austin et al. | 424/401 |
| 5,585,104 | * | 12/1996 | Ha et al. | 424/401 |
| 5,607,980 | * | 3/1997 | McAtee et al. | 514/476 |
| 5,861,145 | * | 1/1999 | Lucas et al. | 424/65 |
| 5,985,931 | * | 11/1999 | Modak et al. | 514/634 |
| 6,019,991 | * | 2/2000 | Tanaka et al. | 424/401 |

FOREIGN PATENT DOCUMENTS

| | | |
|---|---|---|
| 0 370 856 | 5/1990 | (EP) . |
| 0 603 080 | 6/1994 | (EP) . |
| 2 655 265 | 6/1991 | (FR) . |
| WO 86/02001 | 4/1986 | (WO) . |
| 86/02001 * | 4/1986 | (WO) . |
| WO 96/14046 | 5/1996 | (WO) . |

* cited by examiner

Primary Examiner—Yogendra N. Gupta
Assistant Examiner—Charles Boyer
(74) Attorney, Agent, or Firm—Oblon, Spivak, McClelland, Maier & Neustadt, P.C.

(57) ABSTRACT

A cosmetic and/or dermatological composition containing an aqueous phase and a separate oily phase, containing, as preserving agent, poly(hexamethylene biguanide) hydrochloride. The composition is well tolerated by the eyes and stores entirely satisfactorily, while at the same time being in the form of two phases. The composition may be used for cleansing and/or removing make-up from the skin, mucous membranes and/or the eyes, and, most particularly, for removing make-up from sensitive eyes.

16 Claims, No Drawings

TWO-PHASE COSMETIC AND/OR DERMATOLOGIC COMPOSITION WHICH IS USEFUL IN PARTICULAR FOR REMOVING MAKE-UP FROM THE EYES

BACKGROUND OF THE INVENTION

1. Field of the Invention

The present invention relates to a cosmetic and/or dermatological composition comprising an aqueous phase and a separate oily phase, where the composition also contains poly(hexamethylene biguanide) hydrochloride as a preserving agent. The present invention also relates to the use of this composition for cleansing and/or removing make-up from the skin, mucous membranes and/or the eyes, and, in particular, for removing make-up from sensitive eyes.

2. Description of the Background

It is known practice to use compositions which are in the form of two separate phases and which become emulsified by shaking and demix on standing, for removing make-up from the eyes. Such a composition is described, for example, in EP-A-370,856.

These two-phase compositions generally contain preserving agents, in particular quaternary ammonium chlorides such as benzalkonium chloride. However, these compounds occasionally entail tolerance problems, in particular for individuals with sensitive eyes. As a result, it is an important goal to replace these preserving agents with other agents which are better tolerated.

In addition, the preserving agents usually used in compositions in the form of a single phase are often relatively incompatible with the two-phase pharmaceutical form, since these traditional preserving agents lead to physicochemical instabilities giving rise to the formation of a veil or a precipitate in the aqueous phase, or else they greatly disturb the water/oil interface leading to an off-putting appearance of the two-phase composition.

There is thus a need for a two-phase composition which stores well, and does not have the drawbacks of known compositions, i.e., a composition which has both a pleasant appearance and good stability.

SUMMARY OF THE INVENTION

It is an object of the present invention to provide a composition having enhanced stability, where the composition has two phases: an aqueous phase and a separate oily phase.

It is another object of the present invention to provide methods of cleansing and/or removing make-up from the skin, mucous membranes and/or the eyes using the composition described above.

The present inventors have unexpectedly discovered that poly(hexamethylene biguanide) hydrochloride (CTFA name: polyaminopropyl biguanide) gives stable two-phase compositions with good properties of both physicochemical and microbial storage, while at the same time allowing good make-up removal under highly satisfactory conditions of comfort and freshness. There was no indication to suppose that this preserving agent could be used successfully in two-phase compositions.

Accordingly, the objects of the present invention, and others, may be accomplished with a two-phase cosmetic and/or dermatological composition comprising of an aqueous phase and a separate oily phase, where the composition also comprises poly(hexamethylene biguanide) hydrochloride.

The objects of the invention may also be accomplished with a method of preserving a cosmetic composition comprising an aqueous phase and a separate oily phase, comprising incorporating an effective amount of poly(hexamethylene biguanide) hydrochloride into the composition.

The objects of the invention may also be accomplished with a method of cleansing and/or removing make-up from the skin, mucous membranes and/or the eyes, comprising applying the composition to the skin, mucous membranes and/or the eyes.

A more complete appreciation of the invention and many of the attendant advantages thereof will be readily obtained as the same becomes better understood by reference to the following detailed description when considered.

DETAILED DESCRIPTION OF THE INVENTION

Poly(hexamethylene biguanide) hydrochloride is present in the inventive composition in an amount which is sufficient to act as a preserving agent in the composition. Thus, this compound is present in an amount ranging, for example, from 0.01 to 0.5% of the total weight of the composition, and preferably from 0.01 to 0.05% of the total weight of the composition. These ranges include all specific values and subranges therebetween, including 0.02, 0.1, 0.2, 0.3 and 0.4% by weight.

The composition according to the invention comprises at least one aqueous phase (i.e., contains water) and a separate oily phase.

The aqueous phase in the composition of the invention may comprise sterile demineralized water and/or a floral water such as rosewater, cornflower water, camomile water or lime water, or a thermal water or natural mineral water such as, for example: eau de Vittel, waters from the Vichy basin, eau d'Uriage, eau de la Roche Posay, eau de la Bourboule, eau d'Enghien-les-Bains, eau de Saint Gervais-les-Bains, eau de Néris-les-Bains, eau d'Allevar-les-Bains, eau de Digne, eau de Maiziéres, eau de Neyrac-les-Bains, eau de Lons-le-Saunier, Eaux Bonnes, eau de Rochefort, eau de Saint Christau, eau des Fumades, eau de Tercis-les-bains and eau d'Avene. Mixtures of these waters may be used.

The oily phase in the composition according to the invention comprises at least one oil. The oil may be chosen from mineral, plant or synthetic oils or alternatively silicone oils, and mixtures thereof.

Examples of mineral oils which can constitute the oily phase include for example liquid petroleum jelly and higher aliphatic hydrocarbons such as, for example, isohexadecane or isododecane; among the plant oils, jojoba oil and safflower oil; among the silicone oils, which may be volatile, cyclomethicones such as cyclopentadimethylsiloxane, and among the synthetic oils, alkyl palmitates in which the alkyl group contains from 2 to 10 carbon atoms, such as isopropyl palmitate or octyl palmitate, and alkyl adipates in which the alkyl group contains from 2 to 10 carbon atoms, such as bis(2-ethylhexyl) adipate, or any other aliphatic ester containing from 12 to 20 carbon atoms, and mixtures thereof.

According to one specific embodiment of the invention, the oily phase contains at least one oil chosen from alkyl palmitates, isohexadecane, isododecane, volatile silicone oils (cyclomethicones), and mixtures thereof.

When the composition contains an alkyl palmitate, the latter is preferably present in a proportion of at least 5% and, preferably, in a proportion ranging from 8 to 30% of the total weight of the composition. These ranges include all specific values and subranges therebetween, including 6, 10, 12, 15, 20 and 25% by weight.

When the composition contains a volatile silicone oil, the proportion of this oil may range, for example, from 5 to 50% of the total weight of the composition. These ranges include all specific values and subranges therebetween, including 8, 10, 15, 20, 25, 30 and 40% by weight.

According to one preferred embodiment of the invention, the oily phase contains at least isohexadecane or isododecane, or a mixture of these two oils, in a proportion ranging from 5 to 50% and, preferably, 10 to 40% of the total weight of the composition. These ranges include all specific values and subranges therebetween, including 15, 20, 25, 30 and 40% by weight.

The two-phase composition of the invention may be free of surfactant. However, the composition may also comprise at least one surfactant in one or other of the phases.

The surfactant is preferably of the anionic, nonionic or amphoteric type. The surfactant is preferably nonionic. The surfactant is preferably present in the aqueous phase. It is preferably present in a proportion ranging from 0.01 to 10% (of active material) by weight relative to the total weight of the composition, and even more preferably from 0.025 to 3% of the total weight of the composition. These ranges include all specific values and subranges therebetween, including 0.05, 0.075, 0.1, 0.2, 0.5, 1.2, 5 and 8% by weight.

Among the nonionic surfactants, those which are particularly preferred include:

polyoxyethylenated fatty esters of sorbitol, such as the product sold under the name Tween 20® by Atlas.

polyoxyethylenated fatty alcohols, such as the product sold under the name Remcopal 21912 AL® by Gerland.

polyoxyethylenated alkylphenols, such as the product sold under the name Triton X 100® by Rohm-Haas, and condensates of ethylene oxide and of propylene oxide (CTFA name: Poloxamer), such as those sold under the names Synperonic PE® by ICI and in particular those bearing the reference codes L 31, L 64, F 38, F 88, L 92, P 103, F 108 and F 127.

Among the anionic surfactants, suitable examples include:

alkyl ether sulphates, such as the product sold under the name Texapon ASV® by Henkel, alkyl sulphoacetates, such as the products sold under the name Lathanol LAL® by Stepan, alkyl sulphosuccinates, such as the product sold under the name sodium dioctyl sulfosuccinate® by Rhone-Poulenc, alkylamido sulphosuccinates, such as the product sold under the name Rewoderm S 1333® by Rewo, alkylamido polypeptides, such as the product sold under the name Lamepon S® by Gruinau, and acyl sarcosinates, such as the product sold under the name Oramix L 30® by Seppic.

Among the amphoteric surfactants, suitable examples include alkylamidopropyl dimethylbetaines, such as the product sold under the name Tego Betaine L 7® by Goldschmidt, alkylamidobetaines, such as the product sold under the name Incronam 30® by Croda, imidazoline derivatives, such as the product sold under the name Chimexane HD® by Chimex, and N-alkyl-β-iminodipropionates, such as the product sold under the name Monateric ISA 35® by Mona.

The weight ratio between the aqueous phase and the oily phase preferably ranges from 30/70 to 60/40. These ranges include all specific values and subranges therebetween, such as 35/65, 40/60, 45/55, 50/50, and 55/45.

The composition of the invention suitably contains a physiologically acceptable medium, i.e., a medium which is compatible with the skin, mucous membranes and/or the hair.

In addition to the components discussed above, the composition may also contain conventional cosmetic adjuvants, which will be found in one or other phase depending upon their hydrophilic or lipophilic nature, such as, for example, fragrances, dyes, softeners, a buffer, wetting agents, and optionally an electrolyte such as sodium chloride in order to make the aqueous phase isotonic, or any other suitable compound which is compatible with the two-phase composition of the invention.

Among the wetting agents, examples include glycerol, hexylene glycol and polyethylene glycol 600, these agents being present at a concentration of less than or equal to 5% and preferably ranging from 0.05 to 2% relative to the total weight of the composition. These ranges include all specific values and subranges therebetween, such as 0.01, 0.02, 0.1, 0.2, 0.5, 1, 2 and 3% by weight.

Among the softeners, mention may be made in particular of allantoin and certain plant extracts.

The compositions described above can be packaged, as is well-known, in a bottle with a single compartment. In this case, the user may shake the bottle before pouring some of the contents out onto a pad of cottonwool. It is also possible to package two phases of the composition into two separate compartments of the same bottle, with a system being provided for mixing them together at the time of dispensing. Such devices are described, for example, in EP-A-497,256 and FR-A-2,697,233, incorporated herein by reference.

Advantageously, the invention relates to care compositions and in particular compositions for cleansing and/or removing make-up from the skin, mucous membranes such as the lips, and/or the eyes. It is particularly suitable for removing make-up from the eyes when the eyelashes carry mascara, in particular for removing make-up from sensitive eyes, and for removing make-up in the case of long-lasting and/or so-called "transfer-resistant" make-up compositions as described, for example, in FR-A-2,747,566, incorporated herein by reference.

Thus, the invention also includes a process for cleansing and/or removing make-up from the skin, mucous membranes and/or the eyes, by applying the composition to the skin, mucous membranes and/or the eyes. A specific embodiment is a process for removing make-up from sensitive eyes, characterized in that a composition as defined above is applied to the eyes. The composition may, for example, be rubbed on to the area to be treated with the fingers.

Having generally described this invention, a further understanding can be obtained by reference to certain specific examples which are provided herein for purposes of illustration only and are not intended to be limiting unless otherwise specified.

EXAMPLES

The percentages listed below are expressed as percentages by weight.

Example 1

| Two-Phase Composition | |
|---|---|
| Octyl palmitate | 9% |
| Isododecane | 34% |
| Poly(aminopropyl biguanide) | 0.03% |
| Poloxamer 184 (CTFA) | 0.03% |
| Sodium chloride | 0.5% |
| Hexylene glycol | 1% |
| Dyes | qs |
| Demineralized water | qs 100% |

The composition obtained is in two-phase form.

Obviously, additional modifications and variations of the present invention are possible in light of the above teachings. It is therefore to be understood that within the scope of the appended claims, the invention may be practiced otherwise than as specifically described herein.

This application is based on French Patent Application Serial No. 98-08417, filed on Jul. 1, 1998, and incorporated herein by reference in its entirety.

What is claimed is:

1. A two-phase cosmetic and/or dermatological composition having a single water/oil interface, comprising an aqueous phase, a separate oily phase, and poly(hexamethylene biguanide) hydrochloride,
    wherein the oily phase comprises isohexadecane or isododecane, or a mixture of isohexadecane and isododecane, and wherein the isohexadecane or isododecane, or a mixture of isohexadecane and isododecane comprises 5 to 50% by weight of the total weight of the composition.

2. The composition of claim 1, comprising 0.01 to 0.5% by weight of the poly(hexamethylene biguanide) hydrochloride.

3. The composition of claim 1, comprising 0.01 to 0.05% by weight of the poly(hexamethylene biguanide) hydrochloride.

4. The composition of claim 1, wherein the oily phase further comprises at least one oil selected from the group consisting of silicone oils, higher aliphatic hydrocarbons, and synthetic oils.

5. The composition of claim 1, wherein the oily phase further comprises at least one oil selected from the group consisting of alkyl palmitates, volatile silicone oils, and mixtures thereof.

6. The composition of claim 1, wherein the oily phase comprises 10 to 40% by weight of the total weight of the composition.

7. The composition of claim 1, further comprising at least one surfactant.

8. The composition of claim 7, which comprises 0.01 to 10% by weight of the surfactant.

9. The composition of claim 7, wherein the surfactant is anionic, nonionic or amphoteric.

10. The composition of claim 7, wherein the surfactant is selected from the group consisting of polyoxyethylenated fatty esters of sorbitol, polyoxyethylenated fatty alcohols, polyoxyethylenated alkylphenols, condensates of ethylene oxide or propylene oxide, alkyl ether sulphates, alkyl sulphoacetates, alkyl sulphosuccinates, alkylamido sulphosuccinates, alkylamido polypeptides, acyl sarcosinates, alkylamidopropyl dimethylbetaines, alkylamidobetaines, imidazoline derivatives, and N-alkyl-β-iminodipropionates.

11. The composition of claim 1, wherein the weight ratio of the aqueous phase and the oily phase is 30/70 to 60/40.

12. The composition of claim 1, further comprising at least one cosmetic adjuvant.

13. The composition of claim 12, wherein the cosmetic adjuvant is selected from the group consisting of fragrances, dyes, softeners, buffers, wetting agents, and electrolytes.

14. A method of cleansing and/or removing make-up from the skin, mucous membranes and/or the eyes, comprising applying the composition of claim 1 to the skin, mucous membranes and/or the eyes.

15. The method of claim 14, wherein the composition is applied to skin around the eyes.

16. A method of making the composition of claim 1, comprising combining the aqueous phase, oily phase and poly(hexamethylene biguanide) hydrochloride.

* * * * *